(12) United States Patent  (10) Patent No.: US 7,678,251 B2
Chow et al.  (45) Date of Patent: Mar. 16, 2010

(54) SYSTEM AND METHOD FOR DETECTING GAS

(75) Inventors: Oscar Ken Chow, Simsbury, CT (US); Lawrence Clinton Moulthrop, Windsor, CT (US); Ken Wayne Dreier, Madison, CT (US); Jacob Andrew Miller, Dexter, MI (US)

(73) Assignee: Proton Energy Systems, Inc., Wallingford, CT (US)

( * ) Notice: Subject to any disclaimer, the term of this patent is extended or adjusted under 35 U.S.C. 154(b) by 476 days.

(21) Appl. No.: 11/671,594

(22) Filed: Feb. 6, 2007

(65) Prior Publication Data

US 2008/0185297 A1  Aug. 7, 2008

(51) Int. Cl.
*G01N 27/26* (2006.01)
*G01N 27/40* (2006.01)
*G01N 27/404* (2006.01)

(52) U.S. Cl. .............. 204/409; 204/408; 204/415; 204/424; 204/433

(58) Field of Classification Search .............. 204/400, 204/408, 409, 415, 424, 433; 205/780.5, 205/781, 782, 782.5, 783, 785, 785.5, 789, 205/789.5
See application file for complete search history.

(56) References Cited

U.S. PATENT DOCUMENTS

2004/0099045 A1*  5/2004  Demarest et al. .............. 73/23.2
2005/0145494 A1*  7/2005  Inoue et al. .................. 204/431

* cited by examiner

*Primary Examiner*—Bruce F Bell
(74) *Attorney, Agent, or Firm*—Cantor Colburn LLP

(57) ABSTRACT

A system to detect a presence of a specific gas in a mixture of gaseous byproducts comprising moisture vapor is disclosed. The system includes an electrochemical cell, a transport to deliver the mixture of gaseous byproducts from the electrochemical cell, a gas sensor in fluid communication with the transport, the sensor responsive to a presence of the specific gas to generate a signal corresponding to a concentration of the specific gas, and a membrane to prevent transmission of liquid moisture, the membrane disposed between the transport and the gas sensor.

14 Claims, 2 Drawing Sheets

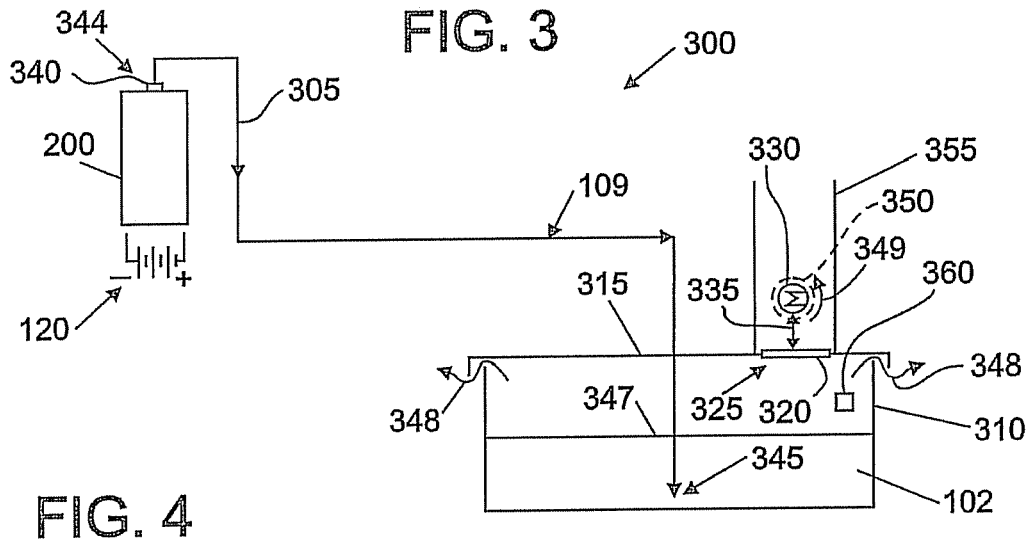
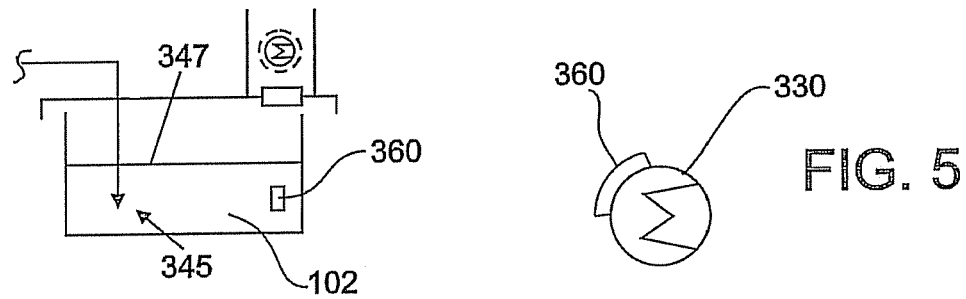
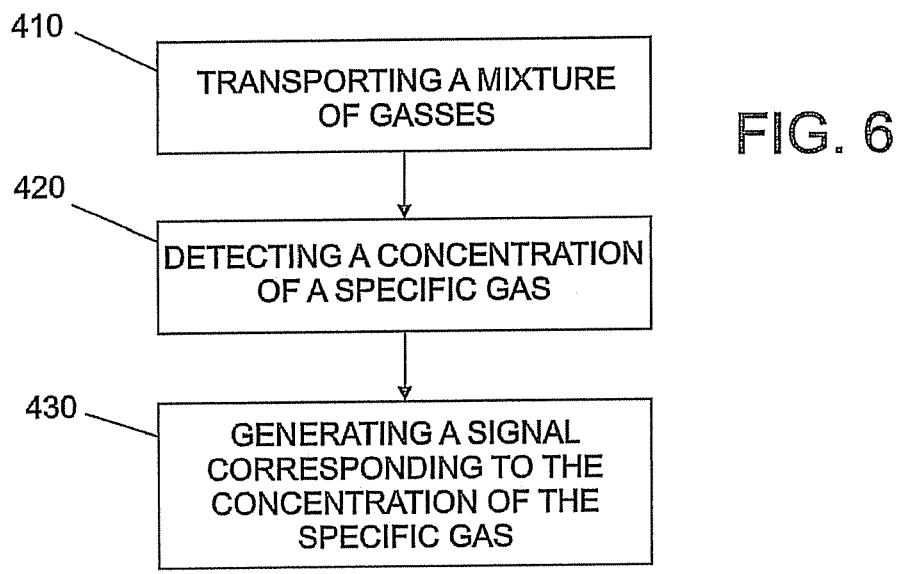

SYSTEM AND METHOD FOR DETECTING GAS

FEDERAL RESEARCH STATEMENT

This invention was made with Government support under prime contract DE-FG36-03GO13063, Sub-Contract RF-05-HFS-005-A02 by the Department of Energy. The Government has certain lights in this invention.

BACKGROUND OF THE INVENTION

The present disclosure relates generally to electrochemical cells, and particularly to sensing gasses that result from operation of electrochemical cells.

Electrochemical cells are energy conversion devices, usually classified as either electrolysis cells or fuel cells. A proton exchange membrane electrolysis cell can function as a hydrogen generator by electrolytically decomposing water to produce hydrogen and oxygen gas, and can function as a fuel cell by electrochemically reacting hydrogen with oxygen to generate electricity. Referring to FIG. 1, which is a partial section of a typical anode feed electrolysis cell 100, process water 102 is fed into cell 100 on the side of an oxygen electrode (anode) 116 to form oxygen gas 104, electrons, and hydrogen ions (protons) 106. The reaction is facilitated by the positive terminal of a power source 120 electrically connected to anode 116 and the negative terminal of power source 120 connected to a hydrogen electrode (cathode) 114. The oxygen gas 104 and a portion of the process water 108 exit the cell 100 as byproducts 109, while protons 106 and water 110 migrate across a proton exchange membrane 118 to cathode 114 where hydrogen gas 112 is produced.

Another typical water electrolysis cell using the same configuration as is shown in FIG. 1 is a cathode feed cell, wherein process water is fed on the side of the hydrogen electrode. A portion of the water migrates from the cathode across the membrane to the anode where hydrogen ions and oxygen gas are formed due to the reaction facilitated by connection with a power source across the anode and cathode. A portion of the process water exits the cell at the cathode side without passing through the membrane.

A typical fuel cell uses the same general configuration as is shown in FIG. 1. Hydrogen, from hydrogen gas, methanol, or other hydrogen source, is introduced to the hydrogen electrode (the anode in fuel cells), while oxygen, or an oxygen-containing gas such as air, is introduced to the oxygen electrode (the cathode in fuel cells). Water can also be introduced with the feed gas. Hydrogen electrochemically reacts at the anode to produce protons and electrons, wherein the electrons flow from the anode through an electrically connected external load, and the protons migrate through the membrane to the cathode. At the cathode, the protons and electrons react with oxygen to form water, which additionally includes any feed water that is dragged through the membrane to the cathode. The electrical potential across the anode and the cathode can be exploited to power an external load.

In other embodiments, one or more electrochemical cells can be used within a system to both electrolyze water to produce hydrogen and oxygen, and to produce electricity by converting hydrogen and oxygen back into water as needed. Such systems are commonly referred to as regenerative fuel cell systems.

Electrochemical cell systems typically include a number of individual cells arranged in a stack, with the working fluids directed through the cells via input and output conduits or ports formed within the stack structure. The cells within the stack are sequentially arranged, each including a cathode, a proton exchange membrane, and an anode. The cathode and anode may be separate layers or may be integrally arranged with the membrane. Each cathode/membrane/anode assembly (hereinafter "membrane-electrode-assembly", or "MEA") typically has a first flow field in fluid communication with the cathode and a second flow field in fluid communication with the anode. The MEA may furthermore be supported on both sides by screen packs or bipolar plates that are disposed within, or that alternatively define, the flow fields. Screen packs or bipolar plates may facilitate fluid movement to and from the MEA, membrane hydration, and may also provide mechanical support for the MEA.

In order to maintain intimate contact between cell components under a variety of operational conditions and over long time periods, uniform compression may be applied to the cell components. Pressure pads or other compression means are often employed to provide even compressive force from within the electrochemical cell.

As a result of normal operating conditions of the anode feed electrolysis cell 100, the oxygen gas 104 and process water 108 produced as byproducts 109 of hydrogen gas 112 generation will include no more than 1%, and typically less than 0.1% hydrogen gas 112. One or more sensors disposed within a stream of the byproducts 109 are used to monitor the stream of the byproducts 109 for the presence of hydrogen gas 112. Excessive or variable flow rate of the stream of byproducts 109 relative to the one or more sensors can disrupt a normal flow in and out of a housing of the sensor and cause erroneous detection. Furthermore, condensation of water vapor 108 included with the oxygen gas 104 upon the sensors has been found to adversely affect reliability, operating life, and detection accuracy of the sensors disposed within the stream of the byproducts 109.

A current practice to reduce condensation of water vapor 108 upon the sensor includes use of at least one of a sampling pump and a cooling means to precondition the stream of the byproducts 109. The sampling pump and cooling means condense water vapor 108 from a sampled stream of the byproducts 109 prior to exposure of the sensor to the sampled stream. Another current practice employs a desiccant to remove water vapor from the sampled stream. Another current practice involves use of a cooling tower, referred to as a "chimney", at the top of which the sensor is disposed. As the sampled stream rises to the top of the chimney, it cools, and leaves condensed moisture behind on the chimney walls. Vacuum pumps and cooling means require additional energy to operate, and employ moving parts that may require additional maintenance. Use of chimneys does not consistently provide sufficient condensation of water vapor 108 under all anticipated operating conditions. Additionally, variable ambient air conditions such as changing temperature and speed external to the sensor as mounted near the chimney exit can adversely affect detection accuracy of the sensor by dilution of the sample. Accordingly, a need exists for an improved gas sensor arrangement that overcomes these drawbacks.

BRIEF DESCRIPTION OF THE INVENTION

An embodiment of the invention includes a system to detect a presence of a specific gas in a mixture of gaseous byproducts comprising moisture vapor. The system includes an electrochemical cell, a transport to deliver the mixture of gaseous byproducts from the electrochemical cell, a gas sensor in fluid communication with the transport, the sensor responsive to a presence of the specific gas to generate a signal corresponding to a concentration of the specific gas, and a membrane to prevent transmission of liquid moisture, the membrane disposed between the transport and the gas sensor.

Another embodiment of the invention includes a method to detect a presence of a specific gas in a mixture of gasses comprising moisture vapor. The method includes transporting the mixture of gasses from an electrochemical cell through a membrane toward a gas sensor, the membrane preventing transmission of liquid moisture to the gas sensor, detecting a concentration of the specific gas via the gas sensor, and in response to the detecting, generating a signal corresponding to the concentration of the specific gas.

A further embodiment of the invention includes an electrochemical cell system. The electrochemical cell system includes an electrochemical cell and a gas detection system. The gas detection system includes a transport to deliver a mixture of gaseous byproducts from the electrochemical cell, a gas sensor in fluid communication with the transport, the sensor responsive to a presence of a specific gas to generate a signal corresponding to a concentration of the specific gas, and a membrane to prevent transmission of liquid moisture, the membrane disposed between the transport and the gas sensor.

These and other advantages and features will be more readily understood from the following detailed description of preferred embodiments of the invention that is provided in connection with the accompanying drawings.

BRIEF DESCRIPTION OF THE DRAWINGS

Referring to the exemplary drawings wherein like elements are numbered alike in the accompanying Figures:

FIG. 3 depicts a schematic diagram of a gas sensing system in accordance with embodiments of the invention;

FIG. 4 depicts a schematic diagram of a gas sensing system in accordance with embodiments of the invention;

FIG. 5 depicts a schematic diagram of a gas sensor in accordance with embodiments of the invention; and FIG. 6 depicts a flowchart of process steps for detecting a presence of a gas in accordance with embodiments of the invention.

DETAILED DESCRIPTION OF THE INVENTION

An embodiment of the invention provides a hydrophobic gas permeable membrane to directly regulate the flow of the stream of byproducts 109 going to the sensor, and eliminate the need for use external pumps, cooling means, and chimneys to precondition the sampled stream of gas. Another embodiment of the invention includes an active heat source to prevent water condensation upon the sensor.

Figure 1:
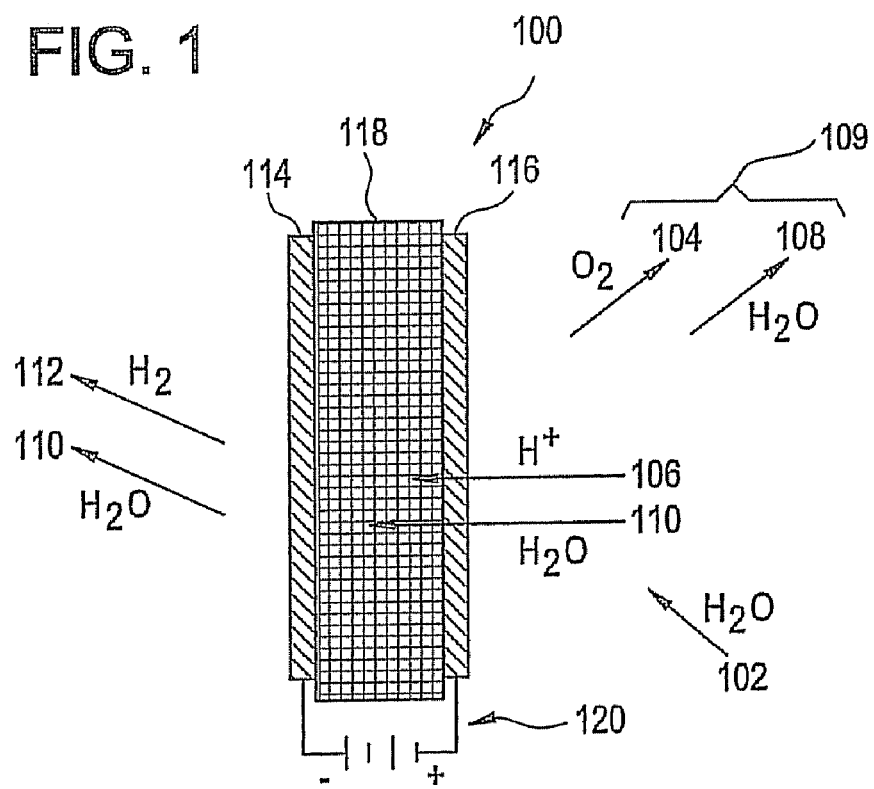
FIG. 1 depicts a schematic diagram of a partial electrochemical cell in accordance with embodiments of the invention.
Figure 2:
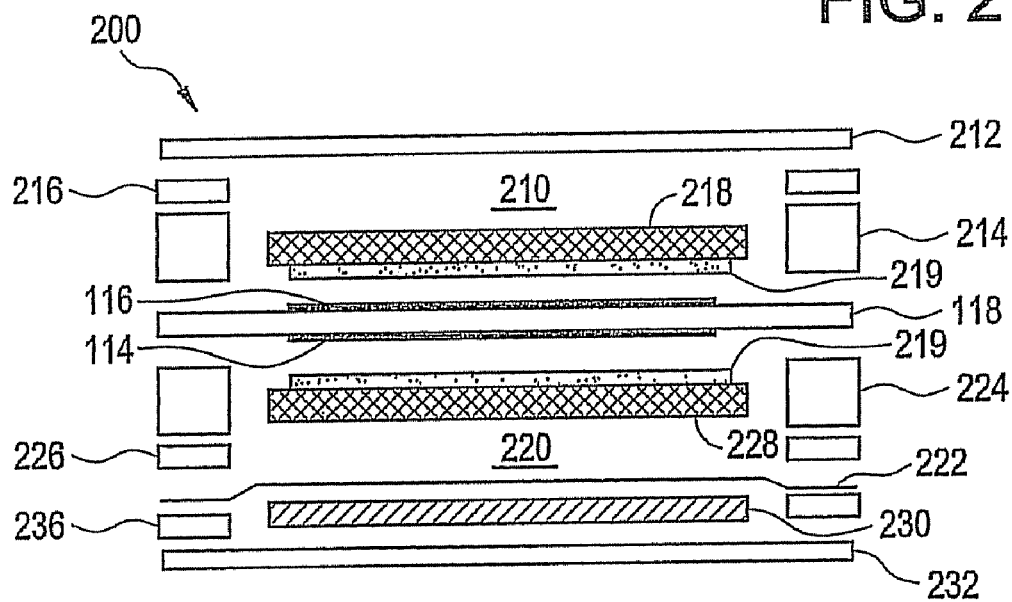
FIG. 2 depicts a schematic diagram of an electrochemical cell system for use in embodiments of the invention.

Referring to FIG. 2, an electrochemical cell 200 that may be suitable for operation as an anode feed electrolysis cell, cathode feed electrolysis cell, fuel cell, or regenerative fuel cell, is depicted schematically in an exploded cross section view. Thus, while the discussion below may be directed to an anode feed electrolysis cell, cathode feed electrolysis cells, fuel cells, and regenerative fuel cells are also contemplated. Cell 200 is typically one of a plurality of cells employed in a cell stack as part of an electrochemical cell system. When cell 200 is used as an electrolysis cell, voltage inputs are generally between about 1.48 volts and about 3.0 volts at current densities between about 50 A/ft2 (amperes per square foot) and about 4,000 A/ft2. When used as a fuel cell, voltage outputs range between about 0.4 volts and about 1 volt, at current densities of about 0.1 A/ft2 and about 10,000 A/ft2. The number of cells within the stack, and the dimensions of the individual cells is scalable to the cell power output and/or gas output requirements. Accordingly, application of electrochemical cell 200 may involve a plurality of cells 200 arranged electrically either in series or parallel depending on the application. Cells 200 may be operated at a variety of pressures, such as up to or exceeding 50 psi (pounds-persquare-inch), up to or exceeding about 100 psi, up to or exceeding about 500 psi, up to or exceeding about 2500 psi, or even up to or exceeding about 10,000 psi, for example.

In an embodiment, cell 200 includes a membrane 118 having a first electrode (e.g., an anode) 116 and a second electrode (e.g., a cathode) 114 disposed on opposite sides thereof. Flow fields 210, 220, which are in fluid communication with electrodes 116 and 114, respectively, are defined generally by the regions proximate to, and bounded on at least one side by, each electrode 116 and 114 respectively. A flow field member (also herein referred to as a screen pack) 228 may be disposed within flow field 220 between electrode 114 and, optionally, a pressure pad separator plate 222. A pressure pad 230 is typically disposed between pressure pad separator plate 222 and a cell separator plate 232. Cell separator plate 232 is disposed adjacent to pressure pad 230. A frame 224, generally surrounding flow field 220 and an optional gasket 226, is disposed between frame 224 and pressure pad separator plate 222 generally for enhancing the seal within the reaction chamber defined on one side of cell system 200 by frame 224, pressure pad separator plate 222 and electrode 114. Gasket 236 may be disposed between pressure pad separator plate 222 and cell separator plate 232 enclosing pressure pad 230.

Another screen pack 218 may be disposed in flow field 210. Optionally, screen packs 218, 228 may include a porous plate 219 as depicted. The porous plate 219 shall preferably be of conductive material, and may be included to provide additional mechanical support to the electrodes 116, 114. A frame 214 generally surrounds screen pack 218. A cell separator plate 212 is disposed adjacent screen pack 218 opposite oxygen electrode 116, and a gasket 216 may be disposed between frame 214 and cell separator plate 212, generally for enhancing the seal within the reaction chamber defined by frame 214, cell separator plate 212 and the oxygen side of membrane 118. The cell components, particularly cell separator plates 212, 232, frames 214, 224, and gaskets 216, 226, and 236 are formed with the suitable manifolds or other conduits as is conventional.

In an embodiment, membrane 118 comprises electrolytes that are preferably solids or gels under the operating conditions of the electrochemical cell. Useful materials include proton conducting ionomers and ion exchange resins. Useful proton conducting ionomers include complexes comprising an alkali metal salt, an alkali earth metal salt, a protonic acid, or a protonic acid salt. Useful complex-forming reagents include alkali metal salts, alkaline metal earth salts, and protonic acids and protonic acid salts. Counter-ions useful in the above salts include halogen ion, perchloric ion, thiocyanate ion, trifluoromethane sulfonic ion, borofluoric ion, and the like. Representative examples of such salts include, but are not limited to, lithium fluoride, sodium iodide, lithium iodide, lithium perchlorate, sodium thiocyanate, lithium trifluoromethane sulfonate, lithium borofluoride, lithium hexafluorophosphate, phosphoric acid, sulfuric acid, trifluoromethane sulfonic acid, and the like. The alkali metal salt, alkali earth metal salt, protonic acid, or protonic acid salt is complexed with one or more polar polymers such as a polyether, polyester, or polyimide, or with a network or cross-linked polymer containing the above polar polymer as a segment. Useful polyethers include polyoxyallylenes, such as polyethylene glycol, polyethylene glycol monoether, and polyethylene glycol diether; copolymers of at least one of these polyethers, such as poly(oxyethylene-co-oxypropylene) glycol, poly(oxyethylene-co-oxypropylene) glycol monoether, and poly(oxyethylene-co-oxypropylene) glycol diether; condensation products of ethylenediamine with the above polyoxyallylenes; and esters, such as phosphoric acid esters, aliphatic carboxylic acid esters or aromatic carboxylic acid esters of the above polyoxyalkylenes. Copolymers of, e.g., polyethylene glycol with diallylsiloxanes, maleic anhydride, or polyethylene glycol monoethyl ether with methacrylic acid are known in the art to exhibit sufficient ionic conductivity to be useful.

Ion-exchange resins useful as proton conducting materials include hydrocarbon- and fluorocarbon-type resins. Hydrocarbon-type ion-exchange resins include phenolic resins, condensation resins such as phenol-formaldehyde, polystyrene, styrene-divinyl benzene copolymers, styrene-butadiene copolymers, styrene-divinylbenzene-vinylchloride telpolymers, and the like, that are imbued with cation-exchange ability by sulfonation, or are imbued with anion-exchange ability by chloromethylation followed by conversion to the corresponding quaternary amine.

Fluorocarbon-type ion-exchange resins may include hydrates of tetrafluoroethylene-perfluorosulfonyl ethoxyvinyl ether or tetrafluoroethylene-hydroxylated (perfluoro vinyl ether) copolymers. When oxidation and/or acid resistance is desirable, for instance, at the cathode of a fuel cell, fluorocarbon-type resins having sulfonic, carboxylic and/or phosphoric acid functionality are preferred. Fluorocarbon-type resins typically exhibit excellent resistance to oxidation by halogen, strong acids and bases. One family of fluorocarbon-type resins having sulfonic acid group functionality is NAFION™ resins (commercially available from E. I. du Pont de Nemours and Company, Wilmington, Del.).

Electrodes 116 and 114 may comprise a catalyst suitable for performing the needed electrochemical reaction (i.e., electrolyzing water and producing hydrogen). Suitable catalyst include, but are not limited to, materials comprising platinum, palladium, rhodium, carbon, gold, tantalum, tungsten, ruthenium, iridium, osmium, alloys thereof, and the like. Electrodes 116 and 114 may be formed on membrane 118, or may be layered adjacent to, but in contact with, membrane 118.

Screen packs 218, 228 support membrane 118, allow the passage of system fluids, and preferably are electrically conductive. The screen packs 218, 228 may include one or more layers of perforated sheets or a woven mesh formed from metal or strands.

Pressure pad 230 provides even compression between cell components, is electrically conductive, and therefore generally comprises a resilient member, preferably an elastomeric material, together with a conductive material. Pressure pad 230 is capable of maintaining intimate contact to cell components at cell pressures up to or exceeding about 100 psi, preferably about 500 psi, more preferably about 2,500 psi, or even more preferably about 10,000 psi. The pressure pads can thus be introduced into a high-pressure electrochemical cell environment. The foregoing is intended for illustration, and not limitation.

Referring now to FIG. 3, an exemplary embodiment of a gas sensing system 300 to detect a presence of a specific gas in a mixture of gasses comprising moisture vapor is depicted. The gas sensing system 300 includes at least one cell 200, a transport 305, such as a pipe, conduit, tubing, or other suitable means to transport the mixture of gasses, also herein referred to as the byproducts 109 of hydrogen gas 112 production, such as oxygen gas 104 and process water 108, for example. The system includes a gas sensor 330 (also herein referred to as a sensor) in fluid communication with the transport 305, the sensor 330 responsive to a presence of the specific gas to generate a signal corresponding to a concentration of the specific gas. The system includes a membrane 320 to prevent transmission of liquid moisture, the membrane 320 being disposed between the transport 305 and the gas sensor 330.

An embodiment includes a holding tank 310 to store process water 102 and a cover 315 disposed upon the holding tank 310 to prevent entry of contaminants into the process water 102. The membrane 320 is disposed upon the cover 315, between the holding tank 310 and the sensor 330, thereby covering an opening 325 of the cover 315. Disposed between the membrane 320 and the sensor 330, is a gap 335. The gap 335 influences a detection accuracy of the sensor 330. In one experimental configuration, a distance of about 3.0 millimeters (mm) provides an optimum accuracy, as will be discussed further below. Alternatively, the holding tank 310 may directly incorporate the opening 325, the membrane 320, and an appropriate venting apparatus.

The specific gas of interest is hydrogen gas 112, because during normal operation of the electrolysis cell 200, excessive amounts of hydrogen gas 112 should not be present in the byproducts 109. In response to an unexpected event within the cell 200, such as a cell membrane rupture for example, or other unexpected event within the system, excessive hydrogen gas 112 may be found to be present within the byproducts 109. In an embodiment, the sensor 330 is responsive to the presence of hydrogen gas 112 within the byproducts 109 to generate a signal corresponding to a concentration of hydrogen gas 112 within a sampled stream 349 of the byproducts 109. Accordingly, the signal corresponding to the concentration of hydrogen gas 112 can be used to determine an operating status of the cell 200. In response to the concentration of hydrogen gas 112 exceeding a pre-determined threshold limit, an appropriate reaction may be performed, such as shutting down operation of the cell 200, for example.

While an embodiment has been described using the sensor 330 responsive to the presence of hydrogen gas 112, it will be appreciated that the scope of the invention is not so limited, and that the invention will also apply to gas sensing systems 300 having sensors responsive to other gasses, such as oxygen, nitrogen, carbon dioxide, carbon monoxide, and others, for example.

The cell 200 includes an appropriate connector 340, such as a fitting, for connection with a first end 344 of the transport 305, such as a length of tubing, for example. The transport 305 transports the byproducts 109 to the holding tank 310. A second end 345 of the transport 305 is disposed beneath a surface 347 of the process water 102. It is desired to transport the byproducts 109 beneath the surface 347 of the process water 102 to attempt to cause a condensation and capture (removal) of as much of the process water 108 as possible. Stated alternatively, the byproducts 109 are bubbled through the process water 102 to attempt to recapture as much of the process water 108 for subsequent reuse as process water 102. Although the byproducts 109 are bubbled through the process water 102, not all of the process water 108 is recaptured, and therefore moisture from process water 108 remains mixed with oxygen 104 within the byproducts 109.

While an embodiment has been described transporting the sampled stream 349 of byproducts 109 to the sensor 330 via a holding tank 310, it will be appreciated that the scope of the invention is not so limited, and that the invention will also apply to gas sensing systems 300 that may utilize a direct transportation of the sampled stream 349, for example.

The membrane 320 is made from a hydrophobic gas permeable material that allows passage of gas, and water in the vapor phase, but prevents passage of water in the liquid phase. In an embodiment, the membrane 320 is made from thermomechanically expanded polytetrafluoroethylene (PTFE), such as GORE-TEX™ (commercially available from W.L. Gore and Associates, Inc., Elkton, Md.). The cover 315 is not sealed to the holding tank 310. Accordingly, subsequent to the byproducts 109 bubbling through the process water 102, the byproducts 109 can be vented to the environment surrounding the holding tank 310, as depicted by reference numerals 348. Additionally, the sampled stream 349 of the byproducts 109 exits the holding tank 310 via the opening 325, through the membrane 320. Because the membrane 320 allows the passage of process water 108 in the vapor phase, it is still possible that process water 108, initially in the vapor phase, can condense (into the liquid phase) upon a surface of the sensor 330. A heater 350 is disposed proximate, or surrounding the sensor 330 and maintains a temperature of the sensor 330 greater than a temperature of at least one of the byproducts 109, the environment surrounding the sensor 330, and the process water 102, thereby preventing condensation of process water 108 upon the sensor 330.

In an embodiment, the sensor 330 is disposed within a housing 355 that directs and retains the sampled stream 349 of the byproducts 109 proximate the sensor 330. In an embodiment, the housing 355 is an integral component of the sensor 330. The membrane 320 will regulate, or reduce the flow, or a diffusion rate through the gas permeable membrane 320 of the sampled stream 349 of the byproducts 109 relative to the sensor 330 disposed within the housing 355. Reducing the diffusion rate of the sampled stream 349 of the by-products 109 relative the sensor 330 will increase a residence time of the byproducts 109 proximate the sensor 330 and thereby increase a detection accuracy of the sensor 330.

The gap 335 between the membrane 320 and the sensor 330 will influence a detection accuracy of the sensor 330. In an exemplary embodiment, the byproducts 109, including a known amount of hydrogen gas 112 equal to about 40% of the lower flammability level (LFL) of hydrogen gas 112 was introduced to the holding tank 310 in a manner as described above. A flow rate of the byproducts 109 including the known amount of hydrogen gas 112 was selected at about 37 liters per minute, with a temperature of the process water 102 maintained at approximately 55 degrees Celsius. The gap 335 was changed, and results of hydrogen gas 112 concentrations generated by the sensor 330 were noted. In response to the gap 335 having a value of approximately 19 mm, the sensor 330 generated a signal corresponding to a presence of hydrogen gas 112 equivalent to 3% to 6% of LFL. In response to the gap 335 having a value of approximately 6.3 millimeters (mm), the sensor 330 generated a signal corresponding to a presence of hydrogen gas 112 equivalent to 12% to 15% of LFL. In response to the gap 335 having a value of approximately 3.0 millimeters (mm), the sensor 330 generated a signal corresponding to a presence of hydrogen gas 112 equivalent to 38% to 40% of LFL. As used herein, the term "approximately" shall refer to a variance from the target value resulting from manufacturing, design, and assembly tolerances.

It has been observed that reducing the value of the gap 335 reduces a dilution of hydrogen gas 112 within the byproducts 109, and results in an increase in the detection accuracy of the sensor 330 used in the gas sensing system 300. Present observations indicate that an elimination of the gap 335, such as below 1.5 mm for example, to close to a zero gap, may have a detrimental effect on the detection accuracy. The gap 335 provides an opportunity for an exchange of the byproducts 109 proximate the sensor 330, and, in the absence of the gap 335, it is contemplated that byproducts 109 are trapped within the housing 355 of the sensor 330, and may degrade the detection accuracy of the sensor 330.

Subsequent to about two hours of testing, it was observed that process water 108 in the vapor phase that had passed through the membrane 320 condenses upon the sensor 330 in the form of liquid process water 108. A cause of condensation of the process water 108 is a temperature of the sensor 330 lower than a temperature of at least one of the byproducts 109, the environment surrounding the sensor 330, and the process water 102 through which the byproducts 109 are bubbled.

In an embodiment, the heater 350 is disposed surrounding the sensor 330 to keep a temperature of the sensor 330 greater than that of at least one of the byproducts 109, the environment surrounding the sensor 330, and the process water 102 through which the byproducts 109 are bubbled. In an embodiment, a temperature sensor 360 is disposed between the transport 305 and the gas sensor 330, the temperature sensor 360 responsive to generate a signal corresponding to a temperature associated with the moisture vapor of the byproducts 109.

In an embodiment, the temperature sensor 360 is disposed within the holding tank 310 above the surface 347 of the process water 102 and generates a signal representative of the temperature of the moisture vapor of the byproducts 109 prior to exposure to the sensor 330. In another embodiment, as depicted in FIG. 4, the temperature sensor 360 is disposed beneath the surface 347, within the process water 102 to generate a signal representative of the temperature associated with the moisture vapor via the temperature of the process water 102 through which the byproducts 109 are bubbled. In another embodiment, as depicted in FIG. 5, the temperature sensor 360 is in thermal communication, such as disposed upon the gas sensor 330, to generate a signal representative of the temperature associated with the moisture vapor via the temperature of the gas sensor 330. The temperature sensor 360 is in signal communication with the heater 350. The heater is responsive to the signal generated by the temperature sensor 360 to maintain the temperature of the sensor 330 greater than that of at least one of the moisture vapor of the byproducts 109, the environment surrounding the sensor 330, and the process water 102 through which the byproducts 109 are bubbled. In an exemplary embodiment, the heater is responsive to the signal generated by the temperature sensor 360 to maintain the temperature of the sensor 330 greater than the dew point of the moisture vapor to prevent condensation upon the sensor 330.

In an exemplary embodiment, use of the heater 350 to maintain the temperature of the sensor greater than that of the byproducts 109 has been tested for periods greater than 46 hours, and found to eliminate condensation upon the sensor 330.

Referring now to FIG. 6, a flowchart 400 of process steps for detecting the presence of the specific gas, such as hydrogen gas 112 in the sampled stream 349 of the mixture of gasses comprising moisture vapor, is depicted.

The process begins with transporting at Step 410 the byproducts 109 from the electrochemical cell 200 through the membrane 320 toward the gas sensor 330, the membrane 320 preventing transmission of liquid moisture to the gas sensor 330. The method proceeds with detecting at Step 420 the concentration of the specific gas via the gas sensor 330, and, in response to the detecting at Step 420, generating at Step 430 the signal corresponding to the concentration of the specific gas.

In an embodiment, the transporting at Step 410 includes transporting the byproducts 109 that include oxygen gas 104 and process water 108, and the detecting at Step 420 includes detecting the concentration of hydrogen gas 112. In an embodiment, the transporting as Step 410 includes passing at least a portion of the byproducts 109 through the hydrophobic gas permeable membrane 320. In another embodiment, the transporting at Step 410 includes releasing at least a portion of the byproducts 109 beneath the surface 347 of the process water 102 from the second end 345 of the transport 305 within the holding tank 310. In another embodiment, the transporting at Step 410 includes passing at least a portion of the byproducts 109 through the membrane 320, the membrane being disposed between the holding tank 310 and the sensor 330.

In another embodiment, the process further includes heating the sensor 330 via the heater 350 to prevent condensation of moisture vapor from forming upon the sensor 330. Another embodiment of the process includes generating the signal corresponding to the temperature associated with the byproducts 109 via the temperature sensor 360. An embodiment further includes in response to the signal corresponding to the temperature associated with the byproducts 109, controlling the heater 350 to control, or regulate the temperature of the gas sensor 330.

In an embodiment, the transporting at Step 410 includes transporting the byproducts 109 across the gap 335 of less than approximately 6.3 millimeters (mm) between the membrane 320 and the sensor 330. In another embodiment, the transporting at Step 410 includes transporting the byproducts 109 across the gap 335 of less than approximately 6.3 millimeters (mm) between the membrane 320 and the sensor 330.

As disclosed, some embodiments of the invention may include some of the following advantages: the ability to reduce condensation upon a gas sensor, thereby increasing a reliability, an operating life, and a detection accuracy of the gas sensor; and the ability to regulate the diffusion flow rate of the byproducts relative to the sensor, thereby increasing a detection accuracy of the gas sensor.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A system to detect a presence of a specific gas in a mixture of gaseous byproducts comprising moisture vapor, the system comprising:
   an electrochemical cell;
   a transport to deliver the mixture of gaseous byproducts from the electrochemical cell;
   a gas sensor in fluid communication with the transport, the sensor responsive to a presence of the specific gas to generate a signal corresponding to a concentration of the specific gas;
   a membrane to prevent transmission of liquid moisture, the membrane disposed between the transport and the gas sensor;
   wherein the electro chemical cell is an electrolysis cell;
   the system further comprises a holding tank comprising process water utilized by the electrolysis cell;
   a first end of the transport is in fluid communication with the electrolysis cell; and
   a second end of the transport is disposed beneath a surface of the process water to bubble the gaseous byproducts through the process water.

2. The system of claim 1, wherein:
   the membrane regulates a flow of the mixture of gaseous byproducts relative to the sensor.

3. The system of claim 1, wherein:
   the membrane is a hydrophobic gas permeable membrane.

4. The system of claim 3, wherein:
   the membrane comprises thermo-mechanically expanded polytetrafluoroethylene. material.

5. The system of claim 1, wherein:
   the membrane is disposed between the holding tank and the gas sensor.

6. The system of claim 1, further comprising:
   a heater disposed proximate the sensor to prevent condensation of moisture vapor upon the gas sensor.

7. The system of claim 6, further comprising:
   a temperature sensor disposed between the transport and the gas sensor, the temperature sensor responsive to generate a signal corresponding to a temperature associated with the moisture vapor.

8. The system of claim 7, wherein:
   the temperature sensor is disposed at least one of:
   beneath the surface of the process water; and
   upon the gas sensor.

9. The system of claim 7, wherein:
   the heater is responsive to the signal to maintain a temperature of the gas sensor greater than the temperature associated with the moisture vapor.

10. A system to detect a presence of a specific gas in a mixture of gaseous byproducts comprising moisture vapor comprising:
    an electrochemical cell;
    a transport to deliver the mixture of gaseous byproducts from the electrochemical cell;
    a gas sensor in fluid communication with the transport, the sensor responsive to a presence of the specific gas to generate a signal corresponding to a concentration of the specific gas;
    a membrane to prevent transmission of liquid moisture, the membrane disposed between the transport and the gas sensor; and,
    wherein the gas sensor is separated from the membrane by a gap less than approximately 6.3 millimeters (mm).

11. An electrochemical cell system comprising:
an electro chemical cell; and
a gas detection system comprising:
a transport to deliver a mixture of gaseous byproducts from the electrochemical cell;
a gas sensor in fluid communication with the transport, the sensor responsive to a presence of a specific gas to generate a signal corresponding to a concentration of the specific gas; and
a membrane to prevent transmission of liquid moisture, the membrane disposed between the transport and the gas sensor;
wherein the electro chemical cell is an electrolysis cell;
the system further comprises a holding tank comprising process water utilized by the electrolysis cell;
a first end of the transport is in fluid communication with the electrolysis cell; and
a second end of the transport is disposed beneath a surface of the process water to bubble the gaseous byproducts through the process water.

12. The system of claim 11, wherein:
the membrane is a hydrophobic gas permeable membrane.

13. The system of claim 11, further comprising:
a heater disposed proximate the sensor to prevent condensation of moisture vapor upon the gas sensor.

14. An electrochemical cell system comprising:
an electro chemical cell; and
a gas detection system comprising:
a transport to deliver a mixture of gaseous byproducts from the electrochemical cell;
a gas sensor in fluid communication with the transport, the sensor responsive to a presence of a specific gas to generate a signal corresponding to a concentration of the specific gas; and
a membrane to prevent transmission of liquid moisture, the membrane disposed between the transport and the gas sensor;
wherein the gas sensor is separated from the membrane by a gap less than approximately 6.3 millimeters (mm).

* * * * *